(12) United States Patent
Dalle et al.

(10) Patent No.: US 6,248,855 B1
(45) Date of Patent: Jun. 19, 2001

(54) METHOD OF MAKING SILICONE-IN-WATER EMULSIONS

(75) Inventors: Frederic Dalle, Le Vieux Cannet (FR); Leon Marteaux, Brussels (BE)

(73) Assignee: Dow Corning S.A., Seneffe (BE)

( * ) Notice: Subject to any disclaimer, the term of this patent is extended or adjusted under 35 U.S.C. 154(b) by 0 days.

(21) Appl. No.: 09/453,142

(22) Filed: Dec. 2, 1999

(30) Foreign Application Priority Data

Dec. 2, 1998 (GB) .................................................. 9826394

(51) Int. Cl.[7] .................................................. C08G 77/06
(52) U.S. Cl. ............................ 528/26; 524/588; 516/53; 528/18; 528/37
(58) Field of Search .................................. 528/17, 18, 26, 528/37, 38; 524/588; 516/53

(56) References Cited

U.S. PATENT DOCUMENTS

| | | |
|---|---|---|
| 4,496,687 * | 1/1985 | Okada et al. . |
| 5,102,930 * | 4/1992 | Nakazato et al. . |
| 5,254,621 * | 10/1993 | Inoue et al. . |
| 5,326,483 | 7/1994 | Halloran et al. ................. 252/174.15 |
| 5,449,560 | 9/1995 | Antheunis et al. .................. 428/447 |
| 6,136,215 * | 10/2000 | Evans et al. . |

* cited by examiner

*Primary Examiner*—Robert Dawson
*Assistant Examiner*—Marc S. Zimmer
(74) *Attorney, Agent, or Firm*—James L. De Cesare

(57) ABSTRACT

A silicone oil-in-water emulsion containing a linear non-crosslinked silicone copolymer is prepared by polymerizing an OH endblocked polydimethylsiloxane monomer with an amine functional trialkoxysilane monomer in the presence of a metal catalyst. However, the polymerization is interrupted by the emulsification of this copolymer, and a carboxylic anhydride is added prior to the emulsification. The resulting emulsions are particularly useful in most personal care applications, and they also have value in textile fiber treatment, leather lubrication, fabric softening, as release agents, in water based coatings, for oil drag reduction, lubrication, and for the facilitation of cutting of cellulose materials.

12 Claims, No Drawings

METHOD OF MAKING SILICONE-IN-WATER EMULSIONS

FIELD OF THE INVENTION

This invention is directed to a method of making an oil-in-water (O/W) emulsion wherein the oil component of the emulsion is a polymer containing a silicon atom. More particularly, the method involves polymerization of an OH endblocked polydimethylsiloxane (PDMS) monomer with an amine functional trialkoxysilane monomer in the presence of a metal catalyst, an interruption of the polymerization reaction by the addition of an acid anhydride, and an emulsification of the resulting copolymer following interruption of the polymerization reaction.

BACKGROUND OF THE INVENTION

Commercial emulsions containing an amine functional polydimethylsiloxane fluid are limited in their market appeal as they are known to contain only relatively low viscosity amine functional polydimethylsiloxane fluids.

In addition, these commercial emulsions may often contain in excess of about one percent of a volatile cyclic species of polydimethylsiloxane such as octamethylcyclotetrasiloxane, in addition to the low viscosity amine functional polydimethylsiloxane fluid, and this content of volatile species is unacceptable according to recent safety and environmental regulations and guidelines.

While higher viscosity polysiloxane polymers with a content of volatile cyclic species less than 0.5 percent have been obtained by reacting certain polysiloxanes with a crosslinking agent in the presence of a catalyst, such chain extensions have been obtained using an OH endblocked PDMS and a dialkoxysilane. This procedure is very slow and often takes weeks in order to reach completion. When such processes have been attempted to be modified in order to speed up the reaction, the use of a trialkoxysilane instead of a dialkoxysilane has led to the production of crosslinked elastomeric materials which are undesirable in many applications.

Where the prior art does refer to an emulsion containing an amine functional polydimethylsiloxane, the patents are either silent as regards the particular viscosity or molecular weight of the amine functional polydimethylsiloxane fluid contained in the emulsion, or where the viscosity or molecular weight of the amine functional polydimethylsiloxane fluid is mentioned, it is significantly below the levels now required in the personal care arena industry-wise. In patents where a higher viscosity or a higher molecular weight of the amine functional polydimethylsiloxane fluid is mentioned, however, the patents are generally silent as to how the emulsion is prepared. One example is U.S. Pat. 5,326,483 (Jul. 5, 1994).

In any event, although the prior art known to applicants is replete with patents relating to various types of cured systems containing high viscosity and high molecular weight polysiloxanes, it is not believed to be generally know to employ a trialkoxysilane in order to polymerize an OH endblocked PDMS in bulk, and to produce by such a procedure, a high molecular weight linear non-crosslinked silicone polymer in emulsion form. This is the essence of the contribution of the present invention.

Moreover, it is not believed to be generally know to conduct a polymerization, and then to interrupt the process of polymerization by addition of an anhydride and emulsification, particularly in this silicone cure system, which is known to be unstable and subject to reversion, i.e., depolymerization or post polymerization. However, by the addition of a low level of a carboxylic anhydride directly into the silicone polymer prior to its emulsification, applicants herein have discovered an efficient means avoid this type of reversion.

BRIEF SUMMARY OF THE INVENTION

It is therefore an object of the present invention to manufacture a silicone polymer utilizing a silicone cure system in which a trialkoxysilane is employed, and to interrupt the polymerization when a desired viscosity has been achieved by a step of acidification and phase inversion emulsification. While this process can be used to make emulsions containing a silicone polymer having a viscosity in the range of from about 1,000 mm$^2$/sec to 1,000,000 mm$^2$/sec, it is most preferred that the silicone polymer in the emulsion have a viscosity generally in the range of about 30,000 mm$^2$/sec to about 500,000 mm$^2$/sec.

Thus, according to the present invention, a linear silicone polymer can be obtained provided there is employed a low amount of trialkoxysilane, and provided the step of interrupting polymerization is carried out when the polymer is still linear. In essence, therefore, the step of anhydride addition and emulsification is used in order to stop the polymerization. Reversion of the polymer is avoided by inclusion of an acid anhydride to the polymer prior to emulsification.

Among some of the benefits obtained according to the present invention are that there can be provided a useful silicone emulsion containing a much higher molecular weight linear amine functional polysiloxane polymer which possesses improved hair conditioning than can be presently obtained with state of the art manufacturing techniques.

In addition, the use of a trialkoxysilane significantly speeds up the polymerization kinetics when compared to techniques employing a dialkoxysilane, and quite unexpectedly, this does not leads to a crosslinked material when the trialkoxysilane is used in low amounts, and polymerization is stopped by anhydride addition and emulsification. While the trialkoxysilane can be used in an amount as high as about 5 percent by weight, it is preferred to use it at a level which is generally less than about 3 percent by weight.

These and other objects, features, and benefits of the present invention will become apparent from a consideration of the following detailed description thereof.

DETAILED DESCRIPTION OF THE INVENTION

The method according to the present invention is carried out in essentially two steps. The first step involves polymerization of an OH endblocked polydimethylsiloxane monomer with an amine functional trialkoxysilane monomer, in the presence of a metal catalyst. In the second step, the condensation reaction occurring in the first step is interrupted by addition of an anhydride, and its emulsification by the addition of a surfactant(s) and water.

The polydimethylsiloxane monomer used in the above reaction in the first step of the process generally comprises a substantially linear polymer of the structure:

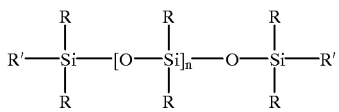

In this structure, each R independently represents a hydrocarbon group having up to 20 carbon atoms, such as an alkyl group, representative of which are methyl, ethyl, propyl, or butyl. R can also be an aryl group such as phenyl. R' represents OH. n is a positive integer greater than one. Preferably n is an integer that results in a polysiloxane with a viscosity between about 1 and about $1\times10^6$ mm$^2$/sec at 25° C.

If desired, the polysiloxane can have a small amount of branching, e.g., less than 2 mole % of the siloxane units, without affecting the invention, i.e., the polymers are substantially linear. Preferably, all of the R groups are methyl groups.

The organosilicon material which reacts with the OH endblocked PDMS in the condensation reaction is an aminotrialkoxysilane. This material can be represented by the formula Q—Si—(OR")$_3$ where R" is an alkyl group containing 1–6 carbon atoms; Q denotes an amine functional substituent of the formula —R'"Z wherein R'" is a divalent alkylene radical of 3 to 6 carbon atoms; and Z is a monovalent radical selected from the group consisting of —NR$_2$"", and —N""(CH$_2$)$_m$NR$_2$"", where R"" denotes hydrogen or an alkyl group of 1 to 4 carbons, and m is a positive integer having a value of from 2 to 6.

Suitable R" groups are represented by and may be independently selected from among methyl, ethyl, propyl, isopropyl, butyl, and isobutyl.

The alkylene radicals represented by R'" may include trimethylene, tetramethylene, pentamethylene, —CH$_2$CHCH$_3$CH$_2$—, and —CH$_2$CH$_2$CHCH$_3$CH$_2$—. Silanes where R'" is a trimethylene or an alkyl substituted trimethylene radical such as —CH$_2$CHCH$_3$CH$_2$—, are preferred.

Useful Z radicals include the unsubstituted amine radical —NH$_2$, alkyl substituted amine radicals such as —NHCH$_3$, —NHCH$_2$CH$_2$CH$_2$CH$_3$, and —N(CH$_2$CH$_3$)$_2$; and aminoalkyl substituted amine radicals such as —NHCH$_2$CH$_2$NH$_2$, —NH(CH$_2$)$_6$NH$_2$, and —NHCH$_2$CH$_2$CH$_2$N(CH$_3$)$_2$.

Some representative commercially available aminotrialkoxysilanes which can be used are 4-aminobutyltriethoxysilane; N-(2-aminoethyl)-3-aminopropyltrimethoxysilane; N-(6-aminohexyl) aminopropyltrimethoxysilane; 3-aminopropyltriethoxysilane; 3-aminopropyltrimethoxysilane; (3-aminopropyl)tris[2-(2-methoxyethoxy)ethoxy]silane; and 3-[2-(2-aminoethylamino)ethylamino]propyl-trimethoxysilane.

If desired, other types of functional trialkoxysilanes can also be used herein, such as epoxyfunctional trialkoxysilanes, acryloxyfunctional trialkoxysilanes, and methacryloxyfunctional trialkoxysilanes, for example. Some representative compositions which can be used include 3-(glycidoxypropyl)trimethoxysilane, [β-(3,4-epoxycyclohexyl)ethyl]trimethoxysilane, 5,6-(epoxyhexyl)trimethoxysilane, 3-(acryloxypropyl)trimethoxysilane, and 3-(methacryloxypropyl)trimethoxysilane.

The metal catalyst for the reaction of the ≡Si—OH with the ≡Si—OR is an organotin salt, some examples of which include stannous octoate, dimethyltin dilaurate, dibutyltin dilaurate, dibutyltin diacetate, dimethyltin dineodecanoate, dibutyltin dimethoxide, isobutyl tin triceroate, dimethyltin dibutyrate, triethyltin tartrate, tin oleate, tin naphthenate, tin butyrate, tin acetate, tin benzoate, tin sebacate, and tin succinate. Generally, the catalyst is used in amounts of between about 0.001 and 10 weight percent based on the weight of the OH endblocked PDMS.

The condensation reaction occurring in the first step of the process, involving the OH endblocked PDMS, the aminotrialkoxysilane, and the metal catalyst, according to this invention, can be generally depicted as seen below:

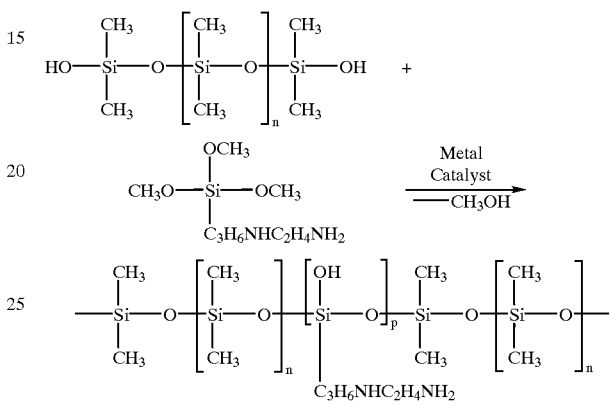

The condensation reaction is also capable of producing a species of OH endblocked amine functional siloxane with a structure generally as shown below:

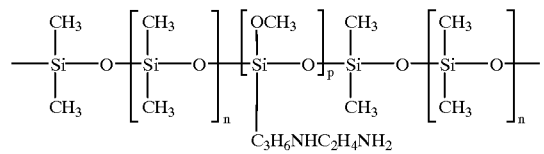

The condensation reaction is interrupted by the addition of an acid anhydride, preferably a carboxylic anhydride, such as acetic anhydride (CH$_3$CO)$_2$O or benzoic anhydride (C$_6$H$_5$CO)$_2$O. Other carboxylic anhydrides can also be used, such as succinic anhydride, phthalic anhydride, and maleic anhydride.

Following this interruption, the resulting linear OH endblocked amine functional siloxane copolymer is emulsified using water and a suitable surfactant or mixture of surfactants.

The surfactant can be a non-ionic surfactant, a cationic surfactant, an anionic surfactant, an alkylpolysaccharide, or an amphoteric surfactant. If desired, a silicone polyether can also be employed.

Examples of non-ionic surfactants include polyoxyalkylene alkyl ethers, polyoxyalkylene sorbitan alkyl esters, polyoxyalkylene alkyl esters, and polyoxyalkylene alkylphenol ethers, polyethylene glycols, polypropylene glycols, and diethylene glycols.

Examples of cationic surfactants include quaternary ammonium hydroxides such as tetramethylammonium hydroxide, cetyltrimethylammonium methosulfate, alkyltrihydroxyethylammonium acetate, octyltrimethylammonium hydroxide, dodecyltrimethyl ammonium hydroxide, hexadecyltrimethyl ammonium hydroxide, octyldimethylbenzylammonium hydroxide, decyldimethylbenzyl ammonium hydroxide, didodecyldimethyl ammonium hydroxide, dioctadecyl dimethylammonium hydroxide, tallow trimethylammonium hydroxide and cocotrimethylammonium hydroxide, as well as corresponding salts of these materials; fatty acid amines and amides and their derivatives, and the salts of the fatty acid amines and amides, including aliphatic fatty amines and their derivatives, homologues of aromatic amines having fatty chains, fatty amides derived from aliphatic diamines, fatty amides derived from disubstituted amines, derivatives of ethylene diamine, amide derivatives of amino alcohols, amine salts of long chain fatty acids, quaternary ammonium bases derived from fatty amides of disubstituted diamines quaternary ammonium bases of benzimidazolines; basic compounds of pyridinium and its derivatives; sulfonium compounds; quaternary ammonium compounds of betaine; urethanes of ethylene diamine; polyethylene diamines; and polypropanol polyethanol amines.

Examples of suitable anionic surfactants include alkyl sulfates such as lauryl sulfate; polymers such as an acrylate/$C_{10-30}$ alkyl acrylate crosspolymer; alkylbenzenesulfonic acids and salts, such as hexylbenzenesulfonic acid, octylbenzenesulfonic acid, decylbenzenesulfonic acid, dodecylbenzenesulfonic acid, cetylbenzenesulfonic acid and myristylbenzenesulfonic acid; the sulfate esters of monoalkyl polyoxyethylene ethers; alkylnapthylsulfonic acid; alkali metal sulforecinates; sulfonated glyceryl esters of fatty acids, such as sulfonated monoglycerides of coconut oil acids, salts of sulfonated monovalent alcohol esters, amides of amino sulfonic acids, sulfonated products of fatty acid nitriles, sulfonated aromatic hydrocarbons, condensation products of naphthalene sulfonic acids with formaldehyde, sodium octahydroanthracene sulfonate; alkali metal alkyl sulfates; ester sulfates; and alkarylsulfonates.

Examples of some suitable alkylpolysaccharide surfactants include, for example, materials of the structure $R^1$—O—$(R^2O)_a$—$(G)_b$ wherein $R^1$ represents a linear or branched alkyl group, a linear or branched alkenyl group, or an alkylphenyl group; $R^2$ represents an alkylene group; G is a reduced sugar; a denotes 0 or a positive integer; and b represent a positive integer. These types of surfactants are described in detail, for example, in U.S. Pat. No. 5,035,832 (Jul. 30, 1991).

Examples of suitable amphoteric surfactants include cocamidopropyl betaine and cocamidopropyl hydroxysulfate.

The above surfactants may be used individually or in combination.

The particle size of the silicone in the emulsion is dependent on, among other factors, the amount and type of surfactant employed. The amount of surfactant used will vary depending on the surfactant, but generally, it is used in an amount of between about 1 and 30 weight percent based on the total weight of the OH endblocked PDMS. The particle size can be from about 0.2 micrometer to about 10 micrometer, but it is preferably from about 0.3 micrometer to about 1.5 micrometer.

The final material used to form the emulsions herein is water, which forms the continuous phase of the emulsion, and into which the silicone oil droplets are dispersed.

If desired, other materials can be added to either phase of the emulsion. For example, perfumes, colorants, thickeners, preservatives, plasticizers, and active ingredients such as pharmaceuticals may be included.

According to the invention, the linear OH endblocked amine functional siloxane copolymer, the surfactant, and water, are mixed by simple agitation to form a coarse water in oil mixture. This mixture is then emulsified. During emulsification, the coarse water in oil mixture is inverted into a fine silicone in water emulsion. The emulsification can be accomplished by conventional means such as a batch mixer, colloid mill or line mixer. The emulsification process is, thus, simple and fast.

The linear OH endblocked amine functional siloxane copolymer, the surfactant, and water, can be mixed all at once or, alternatively, the materials can be mixed in any order, provided that water is the last component.

EXAMPLES

The following examples are set forth for the purpose of illustrating the invention in more detail.

Example 1

A cationic emulsion was prepared by mixing 49.64 gram of an OH endblocked PDMS having a degree of polymerization of about 560, 0.1 gram of a tin catalyst, and 0.26 gram of N-(2-aminoethyl)-3-aminopropyltrimethoxysilane. The tin catalyst used in this example was dimethyltin dineodecanoate. By degree of polymerization is meant that the value of "n" in the formula shown above for the polydimethylsiloxane monomer was about 560. Thus, the polydimethylsiloxane monomer had a structure generally corresponding to the formula $HO(CH_3)_2SiO[(CH_3)_2SiO]_{560}Si(CH_3)_2OH$. An amine functional siloxane polymer with a viscosity of 100,000 $mm^2/s$ was obtained within 35 minutes at 40° C. It was still flowable and was capable of being mechanically emulsified. There was then conducted a phase inversion emulsification in order to stops further polymerization. This was accomplished by adding to the polymer 0.4 gram of acetic anhydride to avoid any reverse depolymerization. This was followed by the addition of 3 gram of Renex 30, 2 gram of Arquad 16–29, and 4 gram of water. Arquad 16–29, it is noted, is a cationic surfactant, and an N-alkyl trimethylammonium chloride. It is a product of Akzo Chemicals, Inc., Chicago, Ill. Renex 30 is a nonionic surfactant with an HLB of 14.5. It is a polyoxyethylene ether alcohol, and a product of ICI Surfactants, Wilmington, Del. The mixture was sheared sufficiently to accomplish the phase inversion, and shearing was continued until there had been obtained a reduction in the particle size to within a range of about 0.3–0.8 micrometer. To the sheared mixture was added 40.6 gram of dilution water.

A rheological study of the polymer prepared and emulsified in this example showed that no crosslinking had occurred. This was evidenced by the fact that the tan delta or the loss factor, which is a ratio of the viscous modulus G" to the elastic modulus G', corresponded to tan deltas for known linear amine functional siloxane polymers of a viscosity of 100,000 $mm^2/s$, which typically have a value of about 10 at 1 hertz (Hz). It should be pointed out that tan delta is a property generally relevant to, and used to characterize crosslinked materials, i.e., elastomers, and its computation and significance is described in detail in U.S. Pat. 5,449,560 (Sep. 12, 1995), for example.

To insure that no further polymerization had continued in the polymer droplets of the emulsion, the polymer was extracted from the emulsion by the classical methanol/hexane breaking technique, and its viscosity was measured. It was found that the viscosity had remained the same as the viscosity of the neat polymer prior to emulsification. A gas chromatography (GC) analysis was conducted in order to determine the presence of any volatile cyclic silicone species which may have formed as a by-product during the procedure, i.e., such as the species octamethylcyclotetrasiloxane ($D_4$). The analysis showed only about 0.1 percent of $D_4$.

Examples 2–4

Example 1 was repeated except that the amount of tin catalyst used in these three examples was 0.2 percent. The amount of N-(2-aminoethyl)-3-aminopropyltrimethoxysilane used in these three examples also differed and this is shown below in Table 1. Examples 2 and 3 used an OH endblocked PDMS having a different degree of polymerization, and this DP is shown in Table 1. Example 4, on the other hand, used a mixture containing 80 percent by weight of an OH endblocked PDMS having a degree of polymerization of about 560, and 20 percent by weight of an OH endblocked PDMS having a viscosity of about 90 $mm^2/s$.

TABLE 1

|  | Example 2 Shorter PDMS DP 472 | Example 3 Longer PDMS DP 945 | Example 4 Blend of 2 PDMS (DP 560/DP 100) |
| --- | --- | --- | --- |
| Amount of Aminosilane | 0.64% | 0.33% | 3% |
| Time to Reach 100,000 $mm^2/s$ | 340 minutes | 38 minutes | 550 minutes |
| Tan Delta at 1 Hz | 8.8 | 10.4 | 2.7 |

Examples 5–7

Example 1 was repeated using the same OH endblocked PDMS but using 0.52 percent by weight of N-(2-aminoethyl)-3-aminopropyltrimethoxysilane. The result obtained by the phase inversion emulsification was a 100,000 $mm^2/s$ amine functional siloxane. These three examples also differed from Example 1 in the type of surfactant that was used in the emulsification, and this is shown below in Table 2. Elfan NS-242, it is noted, is an anionic surfactant, and an ethoxylated alkyl sulfate. It is a product of Akzo Chemicals BV, Amersfoort, The Netherlands.

TABLE 2

|  | Example 5 Cationic Surfactant | Example 6 Nonionic Surfactant | Example 7 Anionic Surfactant |
| --- | --- | --- | --- |
| Name & Amount | ARQUAD 16–29 5% | RENEX 30 4% | ELFAN NS-242 4% |
| Inversion Water Amount | 0% | 4% | 15% |
| Particle Size | 1.5 μm | 0.4 μm | 1 μm |

Examples 8–10

Example 1 was repeated using the same materials. The tin catalyst was used in an amount of 0.2 percent by weight. The amount of N-(2-aminoethyl)-3-aminopropyltrimethoxysilane used in each of these three examples is shown below in Table 3. These examples show the effect of the silane amount on the crosslinking level (materialized by Tan Delta) of a 100,000 $mm^2/s$ copolymer.

TABLE 3

|  | Example 8 0.44% of Aminosilane | Example 9 0.52% of Aminosilane | Example 10 0.62% of Aminosilane |
| --- | --- | --- | --- |
| Time to Reach 100,000 $mm^2/s$ | 450 minutes | 134 minutes | 82 minutes |
| Tan Delta at 1 Hz | 11.8 | 9.9 | 3.7 |

Example 11

In this example, an amine functional siloxane gum, known to have been depolymerized, was used as a standard for purpose of comparison. It had a viscosity of about 85,000 $mm^2/s$, and a tan delta at 1 Hz of about 10.7. An equivalent amine functional siloxane with a viscosity of 85,000 $mm^2/s$, was prepared using the method according to this invention. It had a tan delta of about 13. This indicates that amine functional siloxanes prepared according to the present invention have a more plastic behavior, and are therefore less elastic. This is evidence that there exist a much lower number of branched monomers, and that the method according to the invention leads to the production of more linear-like polymers.

The emulsions of this invention are useful in most standard applications for silicone emulsions. Thus, they are useful for personal care applications, such as hair, skin, mucous, and teeth. In these applications, the silicone is lubricious and will improve the properties of skin creams, skin care lotions, moisturizers, facial treatments such as acne or wrinkle removers, personal and facial cleansers, bath oils, perfumes, fragrances, colognes, sachets, sunscreens, pre-shave and after shave lotions, shaving soaps, and shaving lathers. It can likewise be used in hair shampoos, hair conditioners, hair sprays, mousses, permanents, depilatories, and cuticle coats, to provide conditioning benefits. In cosmetics, it functions as a levelling and spreading agent for pigments, in make-ups, colour cosmetics, foundations, blushes, lipsticks, eye liners, mascaras, oil removers, colour cosmetic removers, and powders. It is likewise useful as a delivery system for oil and water soluble substances, such as vitamins, organic sunscreens, ceramides, and pharmaceuticals. When compounded into sticks, gels, lotions, aerosols, and roll-ons, the emulsions of this invention impart a dry silky-smooth payout.

When used in personal care products, the emulsions are generally incorporated in amounts of about 0.01 to about 50 weight percent, preferably 0.1 to 25 weight percent of the personal care product. They can be added to conventional ingredients for the personal care product selected. Thus, they can be mixed with deposition polymers, surfactants, detergents, antibacterials, antidandruffs, foam boosters, proteins, moisturising agents, suspending agents, opacifiers, perfumes, colouring agents, plant extracts, polymers, and other conventional personal care ingredients.

Beyond personal care, the emulsions of the invention are useful for other applications such as in textile fiber treatment, leather lubrication, fabric softening, release agents, water based coatings, oil drag reduction, lubrication, and facilitation of cutting cellulose materials.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of making a silicone oil-in-water emulsion containing a linear non-crosslinked silicone copolymer comprising
   (A) polymerizing an OH endblocked poly(di)organosiloxane monomer with an amine functional trialkoxysilane monomer in the presence of a metal catalyst;
   (B) adding to the mixture in step (A) a carboxylic anhydrid;
   and (C) subsequently emulsifying the copolymer prepared during polymerization step (A).

2. A method according to claim 1 in which the carboxylic anhydride is selected from the group consisting of acetic anhydride, benzoic anhydride, succinic anhydride, phthalic anhydride, and maleic anhydride.

3. A method according to claim 1 in which the OH endblocked poly(di)organosiloxane monomer comprises a substantially linear polymer of the structure:

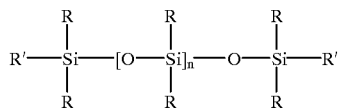

wherein each R independently represents a hydrocarbon group having 1–20 carbon atoms or an aryl group; R' represents OH; and n is a positive integer greater than one.

4. A method according to claim 1 in which the amine functional trialkoxysilane monomer is selected from the group consisting of 4-aminobutyltriethoxysilane; N-(2-aminoethyl)-3-aminopropyltrimethoxysilane; N-(6-aminohexyl)aminopropyltrimethoxysilane; 3-aminopropyltriethoxysilane; 3-aminopropyltrimethoxysilane; (3-aminopropyl)tris[2-(2-methoxyethoxy)ethoxy]silane; and 3-[2-(2-aminoethylamino)ethylamino]propyl-trimethoxysilane.

5. A method according to claim 1 in which the metal catalyst is selected from the group consisting of stannous octoate, dimethyltin dilaurate, dibutyltin dilaurate, dibutyltin diacetate, dimethyltin dineodecanoate, dibutyltin dimethoxide, isobutyl tin triceroate, dimethyltin dibutyrate, dimethyltin dineodecanoate, triethyltin tartrate, tin oleate, tin naphthenate, tin butyrate, tin acetate, tin benzoate, tin sebacate, and tin succinate.

6. A method according to claim 1 in which the copolymer is emulsified using a combination of a nonionic surfactant and a cationic surfactant.

7. A method according to claim 1 in which the copolymer is emulsified using a nonionic surfactant.

8. A method according to claim 1 in which the copolymer is emulsified using a cationic surfactant.

9. A method according to claim 1 in which the copolymer is emulsified using an anionic surfactant.

10. A method according to claim 1 in which the copolymer has a viscosity in the range of from about 30,000 $mm^2$/sec to about 500,000 $mm^2$/sec, and a particle size in the range of from about 0.3 micrometer to about 1.5 micrometer.

11. A method according to claim 1 in which less than about three percent by weight of amine functional trialkoxysilane monomer is used based on the total weight of components used in the polymerization step.

12. A silicone oil-in-water emulsion prepared according to the method defined in claim 1.

* * * * *